(12) United States Patent
Griffin et al.

(10) Patent No.: US 6,241,765 B1
(45) Date of Patent: Jun. 5, 2001

(54) STAPLED HEART PROSTHESIS AND METHOD OF INSTALLING SAME

(75) Inventors: Charles D. Griffin, Leander, TX (US); Arthur A. Alfaro, Collierville, TN (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/353,677

(22) Filed: Jul. 15, 1999

(51) Int. Cl.[7] ............................................. A61F 2/24
(52) U.S. Cl. ........................................... 623/2.38
(58) Field of Search ............................ 523/2.21–2.25, 523/2.38, 2.11

(56) References Cited

U.S. PATENT DOCUMENTS

| | | | |
|---|---|---|---|
| 3,464,065 | * 9/1969 | Chromie | 623/2.35 |
| 4,932,965 | * 6/1990 | Phillips | 623/2.4 |
| 5,397,346 | 3/1995 | Walker et al. | 623/2 |
| 5,397,348 | 3/1995 | Campbell et al. | 623/2 |
| 5,632,433 | 5/1997 | Grant et al. | 227/179.1 |
| 5,641,111 | 6/1997 | Ahrens et al. | 227/175.1 |
| 5,662,258 | 9/1997 | Knodel et al. | 227/175.1 |
| 5,843,179 | * 12/1998 | Vanney et al. | 623/2.4 |
| 6,007,577 | * 12/1999 | Vanney et al. | 623/2.33 |
| 6,042,607 | * 3/2000 | Williamson et al. | 623/2.33 |
| 6,074,418 | * 6/2000 | Buchanan et al. | 623/2.11 |
| 6,096,074 | * 8/2000 | Pedros | 623/2.4 |
| 6,113,632 | * 9/2000 | Reif | 623/2.33 |

* cited by examiner

*Primary Examiner*—David H. Willse
*Assistant Examiner*—Suzette J. Jackson
(74) *Attorney, Agent, or Firm*—Timothy L. Scott

(57) ABSTRACT

A prosthetic heart valve is disclosed which has a rigid shoulder with staple receiving means. Using the staple receiving means of the shoulder, the heart valve may be secured within the heart by stapling the shoulder of the prosthesis to the patient's tissue. Such a prosthesis is advantageous in that it may be secured in a much shorter time period than conventional valves thereby reducing the risks and complications of surgery.

27 Claims, 6 Drawing Sheets

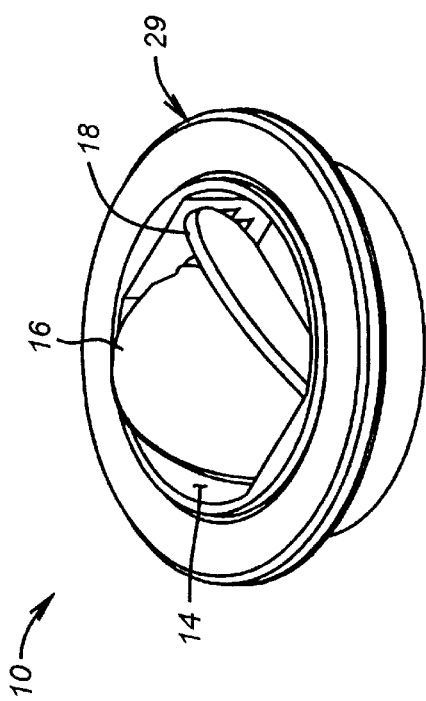
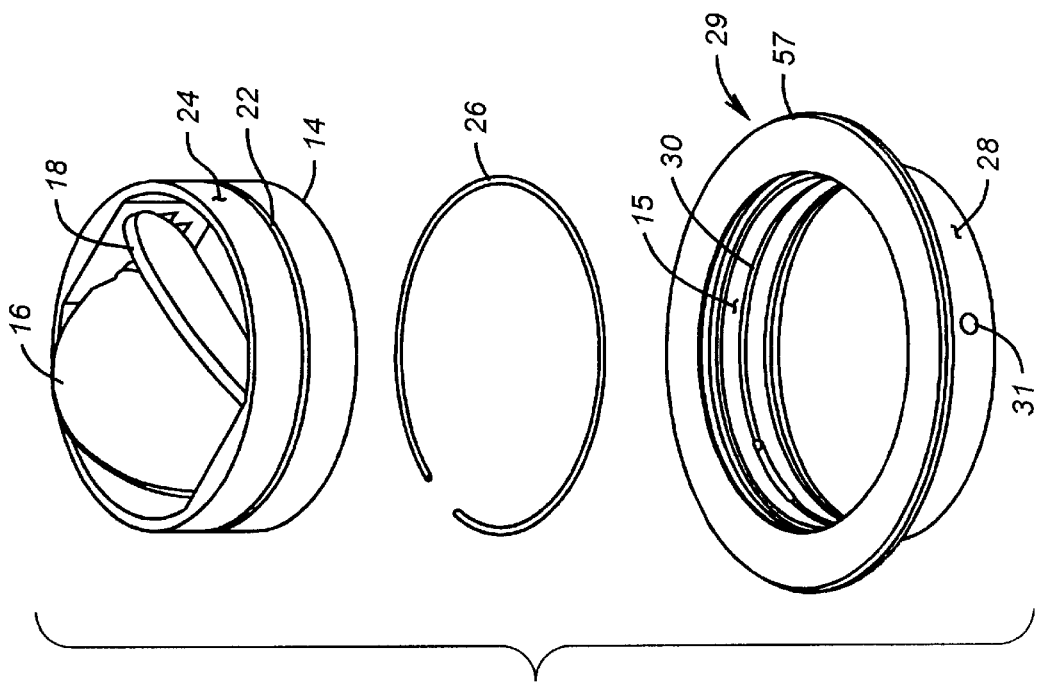

(ENGAGED)

(DISENGAGED)

(ENGAGED)

(DISENGAGED)

STAPLED HEART PROSTHESIS AND METHOD OF INSTALLING SAME

FIELD OF THE INVENTION

The present invention is directed to mechanical prosthetic heart valves, and, more particularly, to a mechanical prosthetic heart valve which may be surgically implanted in the heart of the patient in an expedient manner.

DESCRIPTION OF THE RELATED ART

Mechanical heart valves are conventionally constructed with a rigid annular body supporting one, two, or more leaflets. The action of these leaflets in opening and closing controls the flow of blood through the valve. The annular body of the heart valve is usually secured to what is referred to as a suture ring. The suture ring is generally comprised of a knit fabric tube made from DACRONJ, or some other biocompatible material, which permits a surgeon to sew the heart valve to the patient's heart tissue. Illustrative examples of such suture rings are disclosed in, for example, U.S. Pat. Nos. 5,397,348 and 5,397,346.

It is often necessary to completely remove defective heart valves and replace them with a prosthetic mechanical valve. Installing a mechanical heart valve is a major open heart surgical procedure. The procedure requires general anesthesia and a full cardiopulmonary bypass with complete cessation of cardiopulmonary activity. The invasiveness of the open chest procedure often produces a high degree of trauma and a significant risk of complications that increase the longer that cardiopulmonary activities are stopped. Unfortunately, hand sewing of the replacement heart valve into position using traditional suture rings, such as the suture ring described in U.S. Pat. No. 5,397,348, takes a significant amount of time and skill by the heart surgeon.

For the above reasons, it would be desirable to develop a heart valve and method of insertion therefor which significantly reduces the amount of time for the surgical procedure. It would further be desirable if such a surgical procedure did not require the precision of suturing. The present invention is directed to solving or reducing some of the above-described problems.

SUMMARY OF THE INVENTION

The present invention is directed to an improved mechanical heart valve. The heart valve is comprised of a valve body and a stiffening ring coupled to the valve body. The stiffening ring is comprised of a body and a shoulder. At least one recess is formed in the shoulder, the recess being adapted for engaging at least one staple. The staples are used to secure the stiffening ring to the patient's heart tissue. In another embodiment of the present invention, a plurality of openings are formed in the shoulder, the openings being adapted for receiving a plurality of fasteners in the form of pins that are used to secure the stiffening ring to the patient's heart.

BRIEF DESCRIPTION OF THE DRAWINGS

The invention may be understood by reference to the following description taken in conjunction with the accompanying drawings, in which like reference numerals identify like elements, and in which:

FIG. 2 is a perspective view of an illustrative prosthetic heart valve of the present invention;

FIG. 3 is an exploded, perspective view of the prosthetic heart valve of FIG. 2.

Figure 1:
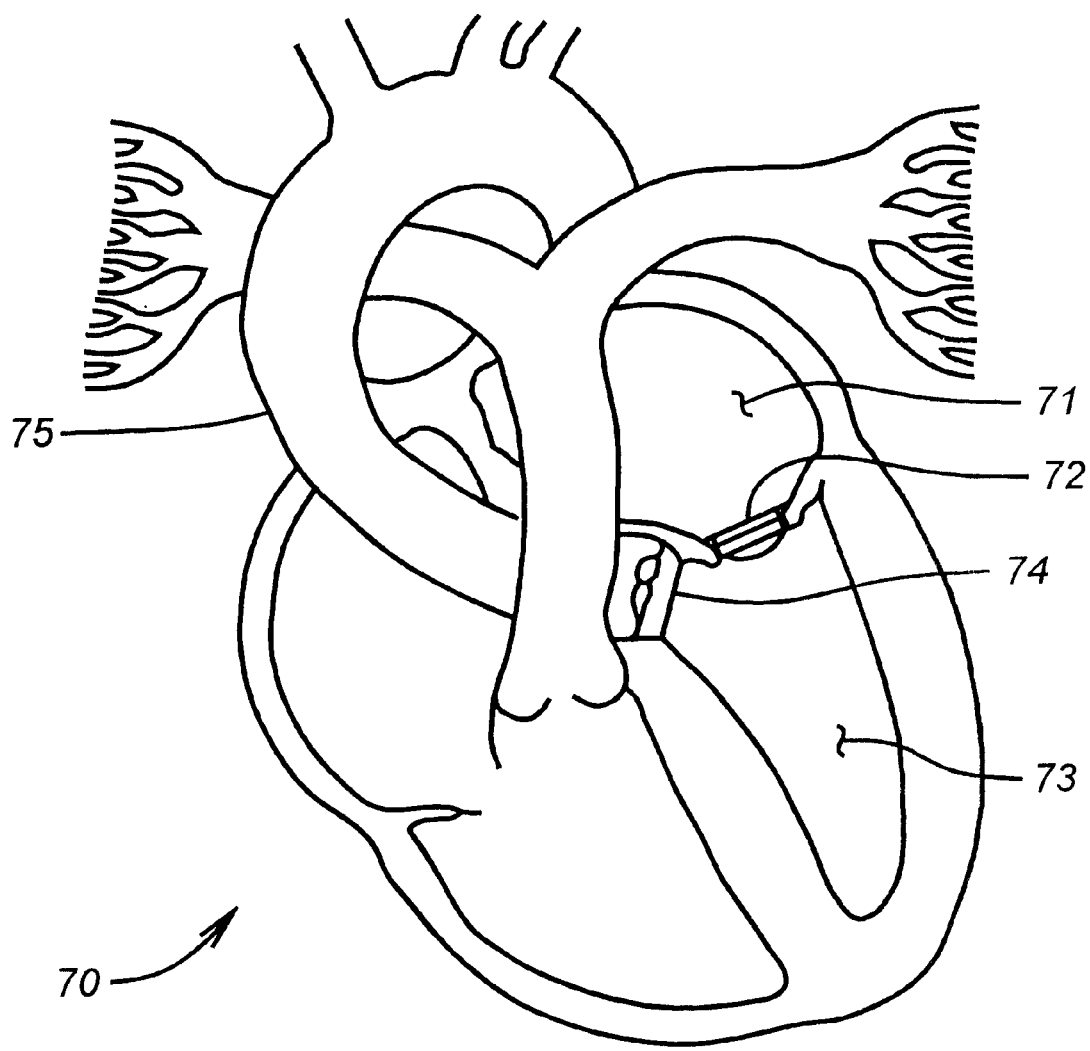
FIG. 1 is a cross-sectional view of a human heart showing the placement of a mitral prosthetic heart valve and an aortic prosthetic heart valve.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers=specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 is a cross-sectional view of a human heart 70 showing the placement of two prosthetic heart valves. A mitral valve 72 is shown positioned between the left atrium 71 and the left ventricle 73 of the heart. An aortic valve 74 is shown positioned between the left ventricle 73 and the ascending aorta 75. Blood flows from the left atrium 71 through the mitral valve 72 into the left ventricle 73. The left ventricle 73 pumps blood through the aortic valve 74 and the ascending aorta 75 to the body.

FIG. 2 is a perspective view of an illustrative example of a prosthetic heart valve, generally designated 10, in accordance with our present invention. The heart valve 10 comprises an annular valve body 14 with pivoting leaflets 16, 18 and a stiffening ring 29. In the embodiment shown, a bileaflet mechanical heart valve is illustrated. Single leaflet and multiple leaflet valves could also be used with our invention. The leaflets generally have a recess and a pivot tab to engage the recess and allow the leaflets 16, 18 to pivot between open and closed positions. A detailed explanation of how such leaflets may be used in the present invention is disclosed in U.S. Pat. No. 5,397,348, which is hereby incorporated by reference in its entirety.

As shown in FIG. 3, the annular valve body 14 has an exterior annular groove 22 on the outer surface 24 of the valve body 14. The groove 22 is adapted to receive a lock wire 26. The illustrative lock wire 26 depicted in FIG. 3 is used to attach the stiffening ring 29 to the annular valve body 14. The illustrative embodiment of the stiffening ring 29 shown in FIG. 3 is comprised of a body 28, a shoulder 57, an opening 31 and a groove 30 formed on the inner surface 15 of the stiffening ring 29. When installed, the illustrative lock wire 26 is inserted through the opening 31 and engages the groove 22 on the valve body 14 and the groove 30 on the body 28 of the stiffening ring 29. Alternative types of devices and techniques for securing the stiffening ring 29 to the valve body 14 are described in U.S. Pat. No. 5,397,346, which is hereby incorporated by reference in its entirety.

Figure 4:
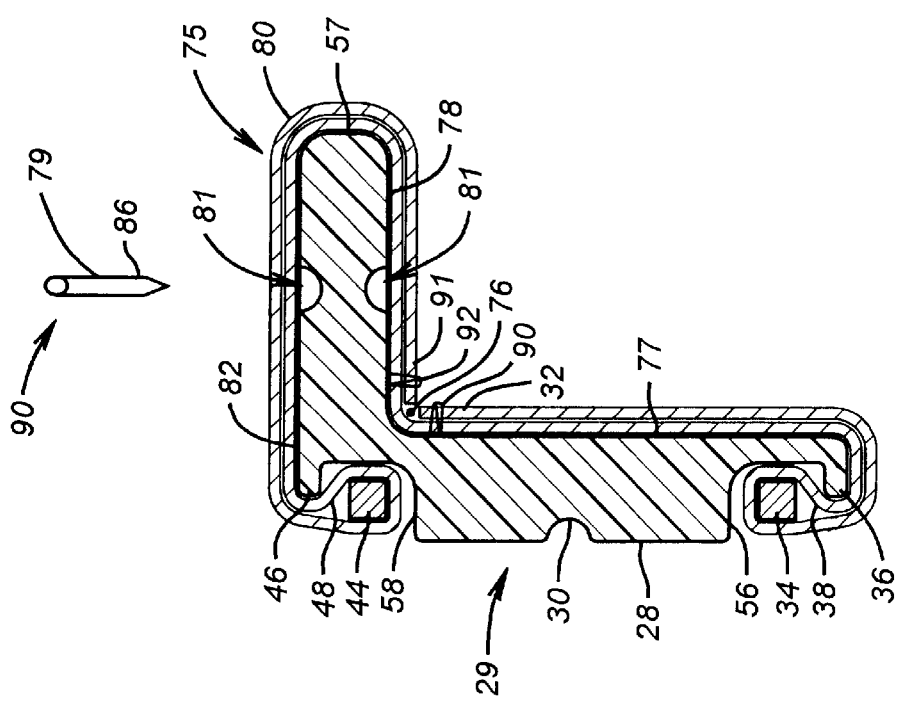
FIG. 4 is a cross-sectional view of an illustrative fabric-covered stiffening ring of the present invention.

As shown in FIG. 4, the angle at which the shoulder 57 extends away from the body 28 of the stiffening ring 29 may be varied as a matter of design choice. For example, the shoulder 57 may be positioned at an angle ranging from approximately 45E to 135E relative to the body 28 of the stiffening ring 29. In one illustrative embodiment, the shoulder 57 extends approximately 90E in a radial direction from the cylindrical body 28 of the stiffening ring 29. The shoulder 57 may be integrally formed with the body 28 of the stiffening ring 29. However, those skilled in the art will appreciate that the shoulder 57 may also be a physically separate component that could be attached to the body 28 of the stiffening ring 29 by any suitable means, including welding, screwed threads, press fitting or any other suitable means. Of course, the shoulder 57 and the body 28 of the stiffening ring 29 may be of different materials of construction depending upon the particular surgical application at issue.

The stiffening ring 29 may be covered with a biocompatible fabric 80 which is usually in the form of a tube 75. The tube 75 may be positioned so as to encompass the stiffening ring 29, and may be attached to the stiffening ring 29 by weaving the fabric around the stiffening ring 29 and between a lower capture ring 34 and an upper capture ring 44. The stiffening ring 29 has an upper recess 58 adapted for receiving an upper capture ring 44 and a lower recess 56 adapted for receiving a lower capture ring 34. In one embodiment, the annular valve body 14 consists of pyrolitic carbon. It is a hard, wear-resistant, biocompatible carbon, well suited for the construction of artificial heart valves. The stiffening ring 29, lock wire 26, and the upper and lower capture rings 44, 34 may be made from a variety of biocompatible materials, such as titanium, cobalt-chromium or the like.

One illustrative technique for wrapping the stiffening ring 29 with a tube 75 comprised of a biocompatible fabric 80 will now be described. The stiffening ring 29 is placed within the tube 75. Although not required, a suture 76 may then be positioned around the exterior surface 77 of the body 28 of the stiffening ring 29 approximately at the location where the shoulder 57 intersects the body 28 as shown in FIG. 4. The suture 76 assists in securing the tube 75 to the stiffening ring 29. Of course, other techniques could be used to accomplish these same results. For example, a ring (not shown) adapted to trap the tube 75 between the ring and the exterior surface 77 of the body 28 could be positioned at the intersection of the body 28 and shoulder 57 to secure the tube 75 to the body 28. Additionally, a groove (not shown) could be formed on the outer surface 77 of the body 28 to retain the ring and/or the suture 76. Any device or method that will assist in securing the fabric tube 75 to the surface 78 of the shoulder 57 and to the outer surface 77 of the body 28 will suffice.

Thereafter, a first end 32 of the tube 75 is wrapped outwardly around the lower edge 36 of the stiffening ring 29, around the lower capture ring 34, and then again around the lower edge 36 of the stiffening ring 29. The wrapped lower capture ring 34 is then placed within the lower recess 56 of the stiffening ring 29. When the first end 32 of the tube 75 is pulled taut, the lower capture ring 34 is secured in the recess 56 of the stiffening ring 29. This crimps the tube 75 between the stiffening ring 29 and the lower ring 34 at a bend 38 of the tube 75 as shown in FIG. 4. The first end 32 of the tube 75 is then secured to the tube 75 by stitches 90, as shown in FIG. 4.

A second end 91 of the tube 75 is then wrapped across the surface 82 of the shoulder 57, around an upper edge 46 of the stiffening ring 29, around the upper capture ring 44, back around the upper edge 46, across the surfaces 82 and 78 of the shoulder 57. The wrapped upper capture ring 44 is then positioned in the upper recess 58. When the second end 91 of the tube 75 is pulled taut, the upper capture ring 44 is pressed up against an upper edge 46 of the stiffening ring 29. This crimps the tube 75 between the stiffening ring 29 and the upper ring 44 at a bend 48 of the tube 75, as shown in FIG. 4. The second end 91 of the tube 75 is then secured to the tube 75 by stitches 92, as shown in FIG. 4.

As shown in FIG. 4, the shoulder 57 has an illustrative recess 81 formed in the surfaces 78, 82. The recess 81 is adapted to engage a device used to secure the stiffening ring 29 within the patient's heart. Although depicted in FIG. 4, it is not necessary to have recesses 81 formed in both the surfaces 78, 82 of the shoulder 57. The number, size, position, and configuration of the recesses 81 may vary depending upon the type of attachment device employed to secure the stiffening ring 29 to the patient's heart. Likewise, the attachment device may vary depending upon the particular patient, heart valve and/or surgeon, etc. Generally, the attachment device will be such that, when installation of the stiffening ring 29 is complete, portions of the tube 75 covering the stiffening ring 29 and the patient's heart tissue remain in sufficient intimate contact such that the patient's heart tissue may grow and intermingle with the fabric 80 positioned around the stiffening ring 29.

In one illustrative embodiment of the present invention, the stiffening ring 29 is secured to the patient's heart tissue by a plurality of fasteners 90 in the form of staples 79. In this embodiment, the recesses 81 formed in the surface 82 and/or the surface 78 of the shoulder 57 are adapted to engage and crimp the staples 79 during the installation procedure. Whether the recesses 81 on the surface 82 or the recesses 81 on the surface 78 of the shoulder 57 are used may depend upon the particular procedure involved, as well as the surgeon=s desired surgical techniques.

Figure 5:
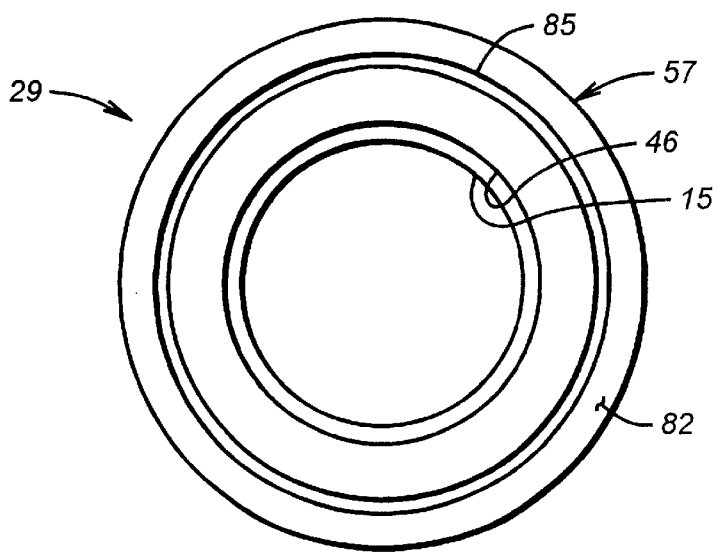
FIG. 5 is a plan view of the shoulder area of a prosthetic heart valve employing one embodiment of the present invention.

The configuration and structure of the recesses 81 may be varied and may be governed by the type of fastener 90 employed. For instance, as shown in FIG. 5, the recesses 81 may be a continuous channel 85 formed in the surface 82 and/or the surface 78 of the shoulder 57. In the illustrative embodiment depicted in FIG. 5, the channel 85 is formed in the surface 82 of the shoulder 57 and extends around the circumference of the shoulder 57 of the stiffening ring 29. Of course, if desired, such a continuous channel 85 could also be formed in the surface 78 of the shoulder 57. In this manner, when a circular stapler is employed, such as that of U.S. Pat. No. 5,533,661, which is hereby incorporated by reference in its entirety, the channel 85 receives the staples 79 and provides a rigid surface to form the staple, i.e., the channel 85 acts to alter the prongs 86 of the staple 79 from their approximately right angle beginning position to their crimped attaching position. Of course, the channel 85 may need not be continuous, it may only extend around a portion of the circumference of the shoulder 57.

Figure 6:
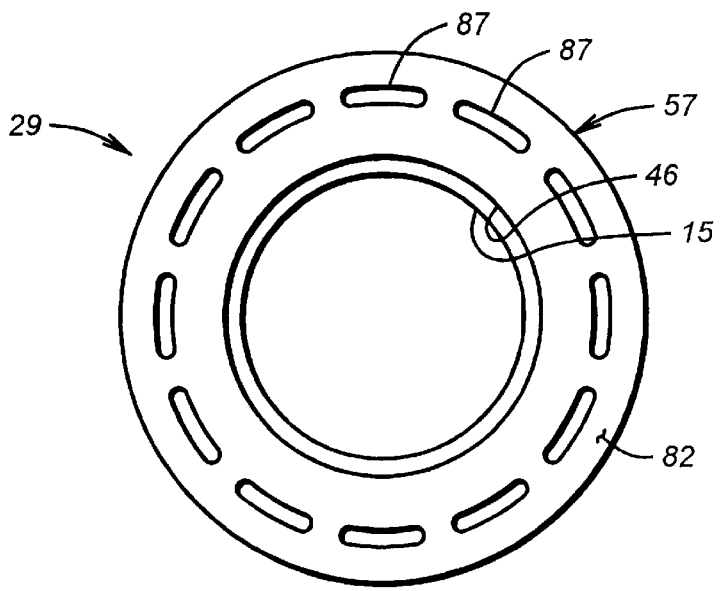
FIG. 6 is a plan view of the shoulder area of yet another prosthetic heart valve employing one embodiment of the present invention.

In another illustrative embodiment of the present invention, as shown in FIG. 6, a plurality of individual recesses 87 may be arranged adjacent to each other around the circumferences of the shoulder 57. As described above, the recesses 87 may be formed on the surface 82, the surface 78 of the shoulder 57, or both, depending on the particular application. Typically, each recess 87 is in positional agreement with the prongs 86 of a staple 79 to be driven through the tube 75 and the tissue of the heart. Each recess 87 preferably has a semicircular indentation in order to assist in forming the staples 79.

Figure 7:
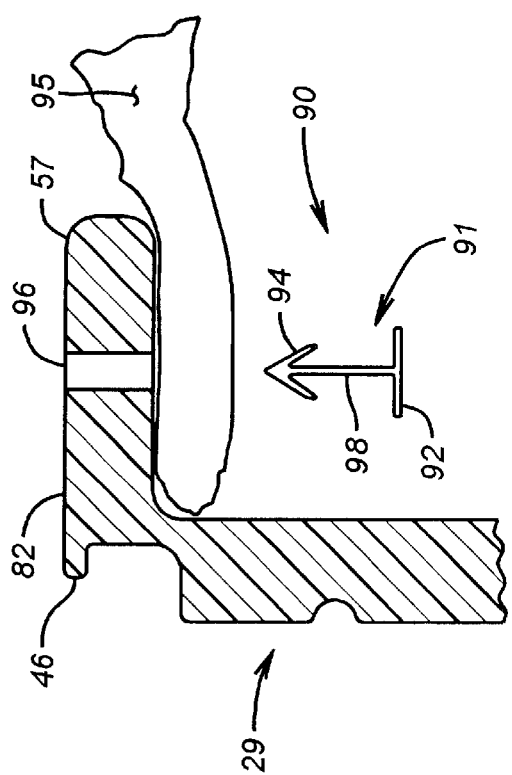
FIG. 7 is a cross-sectional view of the shoulder area of yet another illustrative embodiment of the present invention.

Another alternative technique for attaching the stiffening ring 29 to the patient's heart tissue 95 is shown in FIG. 7. As shown therein, a plurality of openings 96 are formed in the shoulder 57. The openings 96 are adapted to receive a fastener 90 in the form of a pin 91. In one embodiment, the pin 91 is comprised of a flexible barb 94, a shaft 98, and a head 92. In operation, the pin 91 is inserted through the patient's heart tissue 95 and into the opening 96 until the barbs 94 extend through the opening 96 and engage the surface 82 of the shoulder 57. Of course, the openings 96 need not extend completely through the thickness of the shoulder 57.

The size, shape and number of pins 91 used may be varied as a matter of design choice. Additionally, the pins 91 may be made from a variety of materials, such as, for example, stainless steel. As will be recognized by one skilled in the art upon a complete reading of the present application, the fastener 90 may take on a variety of different physical shapes other than the staples 79 and pins 91 specifically disclosed herein. For example, a collection of pins 91 may be configured as a single ring and inserted as a unit into a plurality of openings 96 formed in the shoulder 57. In one illustrative embodiment of the present invention, the stapling of the heart valve into place involves employing a securing device (not shown) which is capable of inserting one or more fasteners 90 through the fabric covering 80 around the stiffening ring 29 and through the tissue of the heart such that the fasteners 90 hold the valve 10 in its proper location. While many devices may be appropriate, a suitable securing device and method of attaching fasteners 90 in the form of stapes 79 is taught in U.S. Pat. No. 5,533,661, where is hereby incorporated by reference in its entirety.

Figure 8:
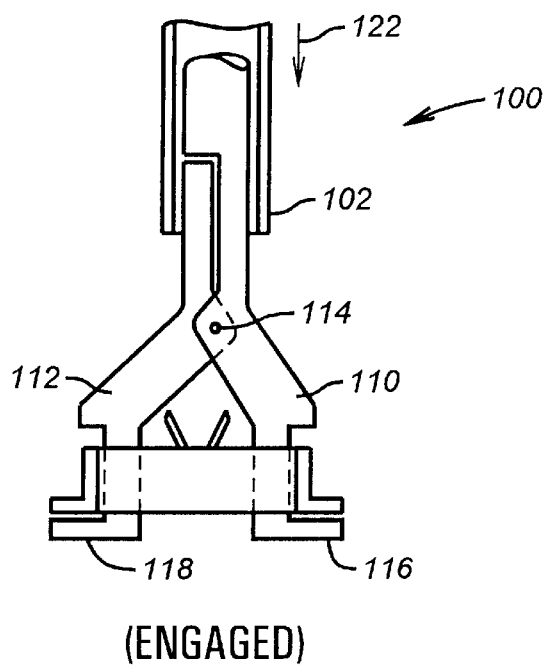
FIG. 8 is an elevation view of an illustrative attachment device that may be used with the present invention.
Figure 9:
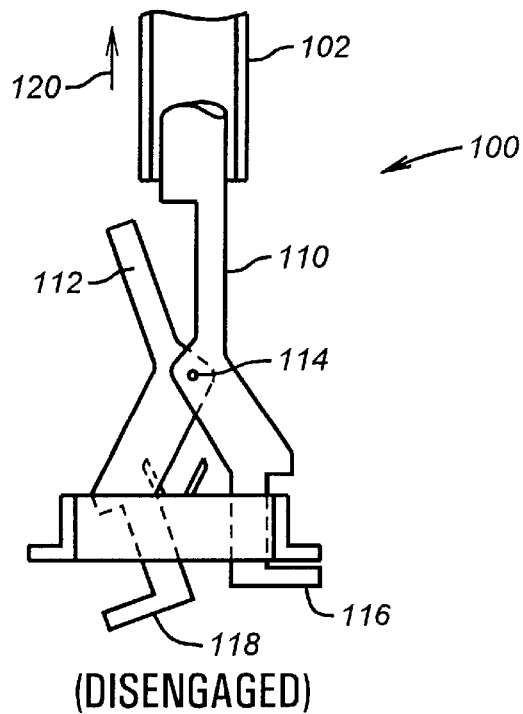
FIG. 9 is another elevation view of the device shown in FIG. 8.
Figure 10:
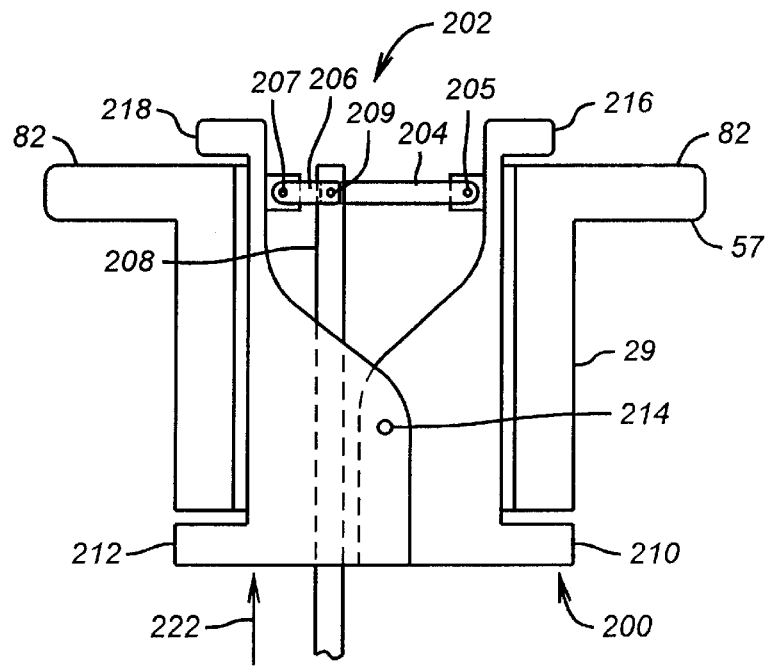
FIG. 10 is an elevation view of another illustrative attachment device that may be used with the present invention.
Figure 11:
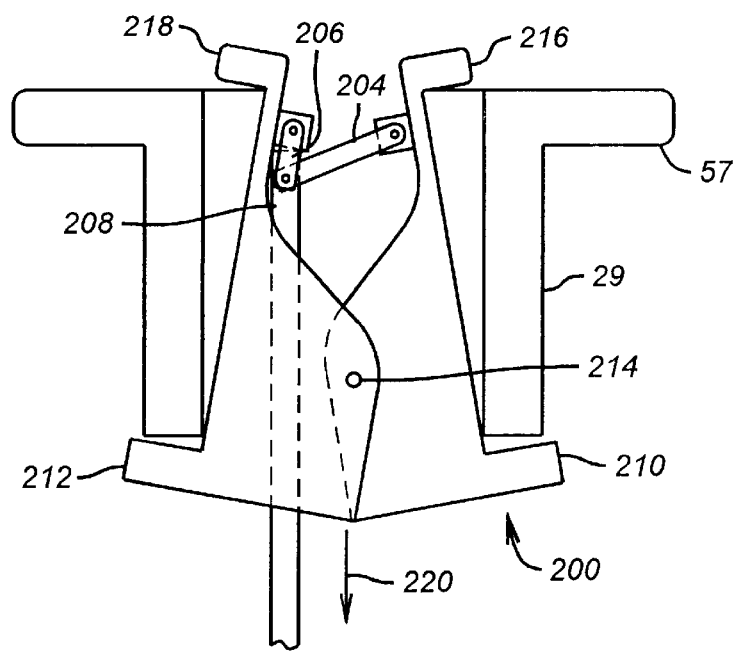
FIG. 11 is another elevation view of the device shown in FIG. 10.

The stiffening ring 29 may be releasably attached to the securing device by a variety of techniques. Whatever means is selected, it should allow for quick and efficient attachment and release of the stiffening ring 29 to the securing device. One illustrative attachment device 100 for releasably securing the stiffening ring 29 to the securing device is shown in FIGS. 8 and 9. Another illustrative attachment device 200 is depicted in FIGS. 10 and 11.

The attachment device 100 may be attached to the securing device (not shown) by a variety of techniques, e.g., screwed threads, welding, snap-on, etc. As shown in FIGS. 8 and 9, the illustrative attachment device 100 is comprised of a first half 110 and a second half 112 that are rotatably coupled together at pin 114. The attachment device 100 is further comprised of lugs 116, 118 that are adapted to engage the surface 82 of the shoulder 57 of the stiffening ring 29. As shown in FIG. 8, the attachment device is further comprised of a locking sleeve 102 that is used to move the attachment device 100 from its engaged position, as shown in FIG. 8, to its disengaged positioned, as shown in FIG. 9.

The locking sleeve 102 is moved in the direction indicated by arrow 122 to engage the attachment device 100 with the stiffening ring 29. This situation is depicted in FIG. 8. The locking sleeve 102 is moved in the direction indicated by arrow 120 to disengage the attachment device 100 from the stiffening ring 29. This situation is depicted in FIG. 9. Note that, due to retraction of the locking sleeve 102 in the direction 120, the attachment device 100 is effectively collapsed thereby allowing the halves 110, 112 to rotate relative to one another to a point such that the lugs 116 and 118 will pass through the stiffening ring 29. The movement of the locking sleeve 102 may be accomplished by withdrawing the sleeve 102 through the securing device (not shown) such that it may be manually actuated by a surgeon during use.

An alternative attachment device 200 may be attached to the securing device (not shown) by a variety of techniques, e.g., screwed threads, welding, snap-on, etc. As shown in FIGS. 10 and 11, the illustrative attachment device 200 is comprised of a first half 210 and a second half 212 that are rotatably coupled together at pin 214. The attachment device 200 is further comprised of lugs 216, 218 that are adapted to engage the surface 82 of the shoulder 57 of the stiffening ring 29. As shown in FIG. 10, the attachment device is further comprised of a mechanical linkage system 202 that is used to move the attachment device 200 from its engaged position, as shown in FIG. 10, to its disengaged positioned, as shown in FIG. 11. The illustrative mechanical linkage system 202 depicted in the drawings is comprised of bars 206 and 204, and actuating rod 208. The bar 206 is pinned to the half 212 at pin 207. The bar 204 is pinned to the half 210 at pin 205. The bars 206, 204 and actuating bar 208 are all pinned together at pin 209.

The actuating bar 208 is moved in the direction indicated by arrow 222 to engage the attachment device 200 with the stiffening ring 29. This situation is depicted in FIG. 10. The actuating bar 208 is moved in the direction indicated by arrow 220 to disengage the attachment device 200 from the stiffening ring 29. This situation is depicted in FIG. 11. Note that, due to retraction of the actuating bar 208 in the direction 220, the mechanical linkage system 202 is effectively collapsed thereby allowing the halves 210, 212 to rotate relative to one another to a point such that the lugs 216 and 218 will pass through the stiffening ring 29. The movement of the actuating bar 208 may be accomplished by extending the bar 208 through the securing device (not shown) such that it may be manually actuated by a surgeon during use.

In operation, after the stiffening ring 29 has been wrapped with the appropriate biocompatible material 80, the stiffening ring 29 is releasably attached to the securing device (not shown) through use of the attachment device 100 described above. Thereafter, the stiffening ring 29 is then positioned within the patient's heart, and the securing device is actuated one or more times to secure the stiffening ring 29 to the patient's heart tissue using a plurality of fasteners 90, such as staples 79 or pins 91. Next, the surgeon disengages the attachment device 100 from the stiffening ring 29 by retraction of the actuating bar 108 in the direction indicated by arrow 120, as shown in FIG. 9. Once released, the securing device and attachment device may be removed from the patient's body. A valve body 14 comprising leaflets 16 and 18 may then be attached to the stiffening ring 29 by insertion of lock wire 26 through the opening 31 in the stiffening ring 29.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A mechanical heart valve assembly, comprising:
   a valve body;
   a stiffening ring coupled to said valve body, said stiffening ring comprised of a body and a shoulder; and
   at least one recess formed in said shoulder, said recess adapted for engaging at least one staple.

2. The mechanical heart valve assembly of claim 1, wherein said shoulder is formed integrally with said body of said stiffening ring.

3. The mechanical heart valve assembly of claim 1, wherein said shoulder and said body of said stiffening ring are physically separate components that are coupled to each other.

4. The mechanical heart valve assembly of claim 3, further comprising means for attaching said physically separate shoulder to said stiffening ring body.

5. The mechanical heart valve assembly of claim 1, wherein said at least one recess is a single continuous recess adapted to engage a plurality of staples.

6. The mechanical heart valve assembly of claim 1, wherein said at least one recess is one of a plurality of separate, non-continuous recesses.

7. The mechanical heart valve assembly of claim 1, wherein said shoulder has a surface and said at least one recess is a continuous recess formed in said surface of said shoulder.

8. The mechanical heart valve assembly of claim 1, wherein said shoulder has a surface and said at least one recess is comprised of a plurality of separate recesses formed in said surface of said shoulder.

9. The mechanical heart valve assembly of claim 1, further comprising a fabric covering positioned around said stiffening ring.

10. The mechanical heart valve assembly of claim 1, wherein said shoulder extends radially away from said body of said stiffening ring at an angle ranging from approximately 45 degrees to 135 degrees relative to said body.

11. The mechanical heart valve assembly of claim 1, wherein said shoulder has an upper surface and said at least one recess is formed in said upper surface of said shoulder.

12. The mechanical heart valve assembly of claim 1, wherein said shoulder has a lower surface and said at least one recess is formed in said lower surface of said shoulder.

13. A mechanical heart valve assembly, comprising:
    a valve body;
    a stiffening ring coupled to said valve body, said stiffening ring comprised of a body and a shoulder; and
    a plurality of recesses formed in a surface of said shoulder, each of said recesses adapted for engaging at least one staple.

14. The mechanical heart valve assembly of claim 13, wherein said surface of said shoulder is an upper surface.

15. The mechanical heart valve assembly of claim 13, wherein said surface of said shoulder is a lower surface.

16. The mechanical heart valve assembly of claim 13, wherein said shoulder extends radially away from said body of said stiffening ring at an angle ranging from approximately 45 degrees to 135 degrees relative to said body.

17. A mechanical heart valve, comprising:
    an annular valve body having an exterior annular groove on an outer surface;
    an annular stiffening ring having a circumferential inner groove, said stiffening ring being circumferentially disposed about said valve body and having a body, an upper recess, a lower recess, and a shoulder extending in a radial direction from the body of the stiffening ring, said shoulder having a staple receiving means;
    an upper capture ring disposed within said upper recess;
    a lower capture ring disposed within said lower recess; and
    a lock wire which is engaged between the exterior annular groove of the annular valve body and the circumferential inner groove of the stiffening ring.

18. The valve of claim 17, wherein the outside diameters of the stiffening ring, upper capture ring, and lower capture ring are within 10 percent of one another.

19. A mechanical heart valve assembly, comprising:
    a valve body;
    a stiffening ring coupled to said valve body, said stiffening ring comprised of a body and a shoulder; and
    a plurality of openings in said shoulder, said openings adapted for receiving a fastener.

20. The device of claim 19, wherein said openings are generally circular.

21. The device of claim 19, wherein said fastener is a pin.

22. The device of claim 19, wherein said fastener is comprised of a pin having a head, a shaft, and a flexible barb.

23. The device of claim 19, wherein said shoulder has a thickness and said fastener has a length that is greater than the thickness of said shoulder.

24. The device of claim 19, wherein said openings extend completely through said shoulder.

25. A mechanical heart valve assembly, comprising:
    a valve body;
    a stiffening ring coupled to said valve body, said stiffening ring comprised of a body and a shoulder; and
    a plurality of openings in said shoulder, said openings adapted for receiving a pin, said pin comprised of a shaft, a head, and a flexible barb.

26. The device of claim 25, wherein said openings are generally circular.

27. The device of claim 25, wherein said shoulder has a thickness and said pin has a length that is greater than the thickness of said shoulder.

* * * * *